US012642967B2

(12) United States Patent
Leonhardt et al.

(10) Patent No.: US 12,642,967 B2
(45) Date of Patent: Jun. 2, 2026

(54) MODULATION OF BRAIN-DERIVED NEUROTROPHIC FACTOR (BDNF)

(71) Applicant: Leonhardt Ventures LLC, Mission Viejo, CA (US)

(72) Inventors: Howard J. Leonhardt, Mission Viejo, CA (US); Kelsie Leonhardt, Mission Viejo, CA (US); Sejal Chaudhari, Holladay, UT (US)

(73) Assignee: Leonhardt Ventures LLC

( * ) Notice: Subject to any disclaimer, the term of this patent is extended or adjusted under 35 U.S.C. 154(b) by 546 days.

(21) Appl. No.: 17/822,690

(22) Filed: Aug. 26, 2022

(65) Prior Publication Data

US 2023/0071154 A1 Mar. 9, 2023

Related U.S. Application Data

(60) Provisional application No. 63/237,682, filed on Aug. 27, 2021.

(51) Int. Cl.
*A61N 1/36* (2006.01)

(52) U.S. Cl.
CPC ...... *A61N 1/36121* (2013.01); *A61N 1/36171* (2013.01); *A61N 1/36175* (2013.01)

(58) Field of Classification Search
CPC ............ A61N 1/36121; A61N 1/36171; A61N 1/36175; A61N 1/326; A61N 1/36025; A61N 1/36034
See application file for complete search history.

(56) References Cited

U.S. PATENT DOCUMENTS

| | | | | |
|---|---|---|---|---|
| 8,442,653 B2 | 5/2013 | Gill | | |
| 10,960,206 B2 | 3/2021 | Leonhardt et al. | | |
| 2018/0064935 A1* | 3/2018 | Leonhardt | .......... | A61N 1/37205 |
| 2020/0230408 A1* | 7/2020 | Errico | ................ | A61N 1/36014 |
| 2020/0289826 A1 | 9/2020 | Leonhardt | | |

OTHER PUBLICATIONS

Feng et al. "Secretion of nerve growth factor, brain-derived neurotrophic factor, and glial cell-line derived neurotrophic factor in co-culture of four cell types in cerebrospinal fluidcontaining medium" Neural Regen Res. Dec. 25, 2012;7(36):2907-14. doi: 10.3969/j.issn.1673-5374.2012.36.008. PMID: 25317143; PMCID: PMC4190949.

(Continued)

*Primary Examiner* — Joseph M Dietrich
(74) *Attorney, Agent, or Firm* — TraskBritt

(57) ABSTRACT

Described is a low voltage, pulsed electrical stimulation device for controlling expression of Brain-Derived Neurotrophic Factor ("BDNF"), a useful protein, by tissues. Also described are methods of enhancing expression of BDNF in cells, particularly a method of stimulating the expression and/or release of BDNF in a cell having a gene encoding BDNF, wherein the method includes applying a bioelectric signal of from about 10 Hz to about 100 Hz (e.g., 5 Hz, 10 Hz, 40 Hz, 100 Hz, or 110 Hz) to the cell (e.g., directly, indirectly, or wirelessly). Applications in the treatment of Alzheimer's disease, depression, schizophrenia, and post-traumatic stress disorder are also disclosed.

14 Claims, 8 Drawing Sheets

(56) References Cited

OTHER PUBLICATIONS

Jiao et al. "Brain-derived neurotrophic factor protects against tau-related neurodegeneration of Alzheimer's disease" Transl Psychiatry. Oct. 4, 2016;6(10):e907. doi: 0.1038/tp.2016.186. PMID: 27701410; PMCID: PMC5315549.

Sato et al. "White matter activated glial cells produce BDNF in a stroke model of monkeys." Neurosci Res. Sep. 2009;65(1):71-8. doi: 10.1016/j.neures.2009.05.010. Epub Jun. 6, 2009. PMID: 19501123.

Wu et al. "Serum Levels of FGF21, β-Klotho, and BDNF in Stable Coronary Artery Disease Patients with Depressive Symptoms: A Cross-Sectional Single-Center Study" Front. Psychiatry, Jan. 21, 2021; https://doi.org/10.3389/fpsyt.2020.587492.

Xiong et al. "Neurotrophins induce BDNF expression through the glutamate receptor pathway in neocortical neurons" Neuropharmacology. Jun. 2002; 42(7): 903-912.

* cited by examiner

MODULATION OF BRAIN-DERIVED NEUROTROPHIC FACTOR (BDNF)

CROSS-REFERENCE TO RELATED APPLICATION

This application claims the benefit under 35 U.S.C. § 119 to U.S. Provisional Patent Application Ser. No. 63/237,682 filed on Aug. 27, 2021, the contents of the entirety of which is incorporated herein by this reference.

TECHNICAL FIELD

The application relates generally to the field of medical devices and associated methods of treatment, and more specifically to methods of treatment involving the precise bioelectrical stimulation of a subject's tissue, optionally augmented with the administration of a composition comprising, among other things, stem cells and nutrients, useful to increase the expression and/or release of brain-derived neurotrophic factor ("BDNF") to stimulate and treat the subject, the subject's tissue(s), the subject's organ(s), and/or the subject's cells. More specifically, the application relates to a device, programmed bioelectric signaling sequences, and associated methods for the controlled expression of secreted BDNF via precise bioelectrical signaling sequences.

BACKGROUND

Brain-derived neurotrophic factor (BDNF) or abrineurin is a key protein involved in plastic changes related to learning and memory. It is encoded by the BDNF gene. BDNF has been linked to enhancing memory by increasing the number, size, and complexity of dendritic spines. Neurogenesis is increased through changes in cell survival and proliferation with BDNF. However, with age, cellular and metabolic changes lead to a reduction of synaptic plasticity in the brain regions.

Cells that produce BDNF include neurons and glia. BDNF expression is induced by other neurotrophins in a joint effort to exert various functions in the neocortex of the brain. BDNF's expression is regulated also by glutamate receptors, where intracellular kinases can differentially participate (Xiong et al. "Neurotrophins induce BDNF expression through the glutamate receptor pathway in neocortical neurons" *Neuropharmacology.* 2002 June; 42(7): 903-912).

In the case of white matter, it has been demonstrated that high levels of expression occur during ischemia (Sato et al. "White matter activated glial cells produce BDNF in a stroke model of monkeys." *Neurosci Res.* 2009 September; 65(1):71-8. doi: 10.1016/j.neures.2009.05.010. Epub 2009 Jun. 6. PMID: 19501123.) and in vitro, several not neuronal, but myelin-forming cells and endothelial cells in co-culture can consistently express BDNF and other growth factors (Feng et al. "Secretion of nerve growth factor, brain-derived neurotrophic factor, and glial cell-line derived neurotrophic factor in co-culture of four cell types in cerebrospinal fluid-containing medium" *Neural Regen Res.* 2012 Dec. 25; 7(36):2907-14. doi: 10.3969/j.issn.1673-5374.2012.36.008. PMID: 25317143; PMCID: PMC4190949). See, also, Jiao et al. "Brain-derived neurotrophic factor protects against tau-related neurodegeneration of Alzheimer's disease" *Transl Psychiatry.* 2016 Oct. 4; 6(10):e907. doi: 10.1038/tp.2016.186. PMID: 27701410; PMCID: PMC5315549.

BRIEF SUMMARY

Described herein is a bioelectric stimulator particularly configured to modulate (e.g., upregulate or downregulate) the expression and/or release of brain-derived neurotrophic factor in cellular tissue.

Also described is a method for treating or regenerating a tissue in a subject (e.g., in an animal, mammal or human), the tissue selected from the group consisting of muscle, heart, eye, liver, dental tissue and teeth, bone, adrenal gland, pancreas, brain, skin, and lung, the method comprising: applying a bioelectric signal to the tissue, which the bioelectric signal regulates (e.g., upregulates or downregulates) the expression and/or release of BDNF.

In certain embodiments, the bioelectric stimulator is further configured to activate expression and/or release of another protein, such as klotho.

Also described is a bioelectric stimulator including: a power source (e.g., battery, capacitor, AC, or other suitable source of electricity), and means for delivering an electrical signal to a subject's cellular tissue (e.g., via electrode(s) or wirelessly). Preferably, such a bioelectric stimulator utilizes the electrical signal to precisely control BDNF expression in the tissue on demand.

In certain cases, the bioelectric stimulator is programmed to produce a bioelectric signal that stimulates target tissue to express and/or release BDNF by the target tissue by utilizing a bioelectric signal at from 1 Hz to 100 Hz (at, e.g., 2 mA) for about an hour of stimulation. Preferred bioelectric signals are at 10 Hz, 40 Hz, 80 Hz, and 100 Hz. Especially preferred are at 10 Hz and 100 Hz.

As used herein, the term "about" when used in conjunction with a number generally means the number plus or minus five percent (5%).

One bioelectric signal for use with mammals to promote the survival of nerve cells, and enhance growth, maturation, and maintenance of cells upregulates expression of BDNF and is a biphasic signal of (within 15%) 10 Hz and 300 μsec pulse width, preferably applied for at least five (5) minutes.

Treatment times with the described bioelectric signal(s) typically range from 5 minutes to more than an hour per treatment session.

In certain embodiments, bioelectric stimulation of the gray matter of porcine neocortex exhibited enhanced expression of BDNF with the application of bioelectric signals at each of 1 Hz, 40 Hz, and 100 Hz, 2 mA, stimulated each for 60 minutes.

In certain cases, the bioelectric stimulator is programmed to produce a bioelectric signal that (after about 20 minutes) downregulates the target tissue to decrease expression and/or release of BDNF by the target tissue by utilizing a bioelectric signal at (a) 10 Hz, 300 μsec pulse width, and 2 mA (as determined at the level of the stimulated cell), (b) 20 Hz, 300 μsec pulse width, and 2 mA (as may be measured at the level of the stimulated cell), (c) 30 Hz, 1,000 μsec pulse width, and 2 mA (as may be measured at the level of the stimulated cell), or (d) 30 Hz, 300 μsec pulse width, and 2 mA (as may be measured at level of the stimulate cell).

Similar bioelectric signals of (i) 10 Hz, 300 μsec pulse width, and 2 mA (as determined at the level of the stimulated cell), (ii) 20 Hz, 300 μsec pulse width, and 2 mA (as may be measured at the level of the stimulated cell), (iii) 30 Hz, 1,000 μsec pulse width, and 2 mA (as may be measured at the level of the stimulated cell), (iv) 20 Hz, 1,000 μsec pulse width, and 2 mA (as may be measured at level of the stimulated cell), and (v) 3 mA direct current (DC) operate to upregulate the expression of growth differentiation factor 10 (GDF10) by the target tissue with 20 minutes of stimulation.

A bioelectric signal of 30 Hz, 300 μsec pulse width, and 2 mA (as may be measured at level of the stimulated cell) operate to downregulate the expression of BDNF, GDF10, and klotho.

A preferred system includes: a bioelectric stimulator that controls/stimulates the release/production of BDNF by a target cell or tissue. The stimulator may be associated with (e.g., connected to) the organ or tissue to be treated with a pacing infusion lead (available from Nanoscribe of Eggenstein-Leopoldshafen, Germany) or wirelessly. In certain cases, the interface with the subject's tissue may be by a conductive soft wrap.

The stimulator can be designed to externally deliver all bioelectric signals wirelessly to the subject's organ(s), tissue (s), and/or cells. In certain embodiments, a micro infusion pump may be included in the system to deliver other supportive substances (such as stem cells) in greater volume more quickly.

While not intending to be bound by theory, the described system utilizes precise bioelectric signaling sequences that appear to communicate with the cells, cell membranes, and DNA of the subject to cause the cells to produce high volumes of the brain-derived neurotrophic factor protein. Indications include treatment and prevention of Alzheimer's disease, treatment and/or prevention of schizophrenia, treatment and/or preventions of post-traumatic stress disorder, treatment and/or prevention of addiction(s), and treatment and/or prevention of depression.

DETAILED DESCRIPTION

In certain embodiments, described is a low voltage, pulsed electrical stimulation device for modulating expression of brain-derived neurotrophic factor ("BDNF"), a useful protein, by tissues. Also described are methods of enhancing expression of BDNF in cells, particularly a method of stimulating the expression and/or release of BDNF in a cell having a gene encoding BDNF, wherein the method includes applying a bioelectric signal of from about 1 Hz to about 100 Hz (e.g., 1 Hz, 5 Hz, 10 Hz, 40 Hz, 100 Hz, or 110 Hz) to the cell (e.g., directly, indirectly, or wirelessly). Applications in the treatment of Alzheimer's disease, depression, schizophrenia, and post-traumatic stress disorder are also disclosed.

Figure 1:
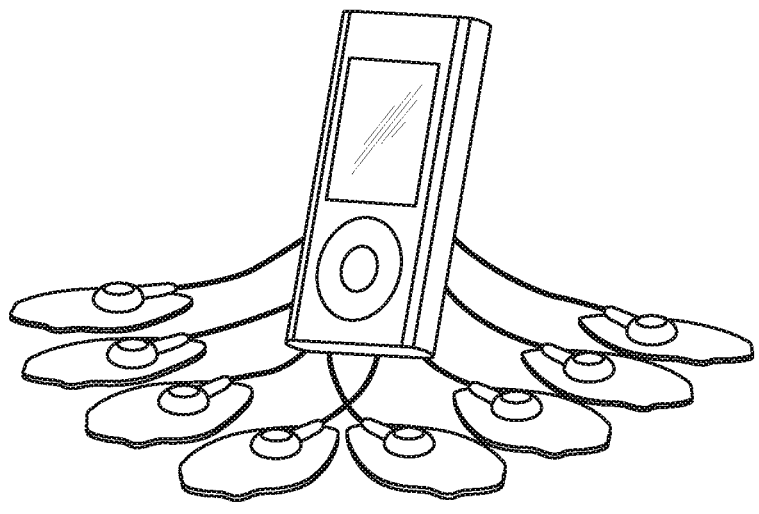
FIG. 1 depicts a programmed bioelectric stimulator for delivery to a subject connected to multiple soft conductive electrode pads.
Figure 2:
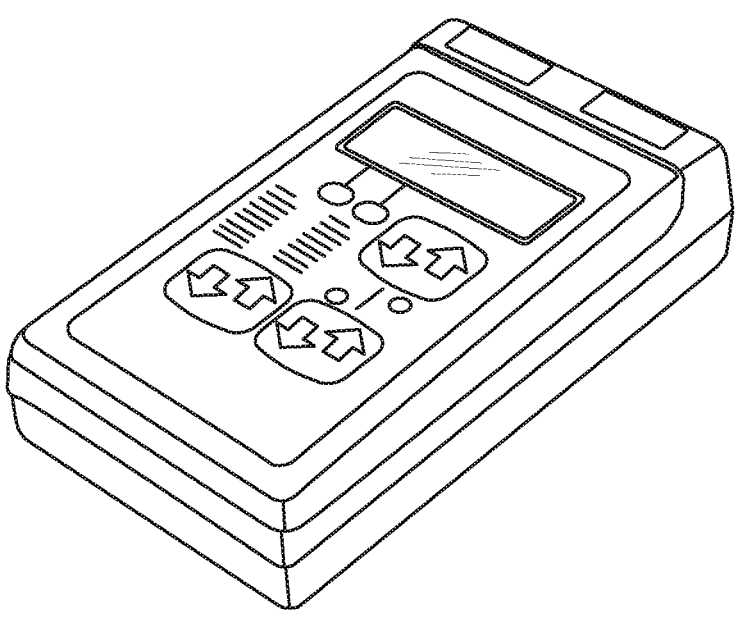
FIG. 2 depicts a programmed bioelectric stimulator as described herein.
Figure 3:
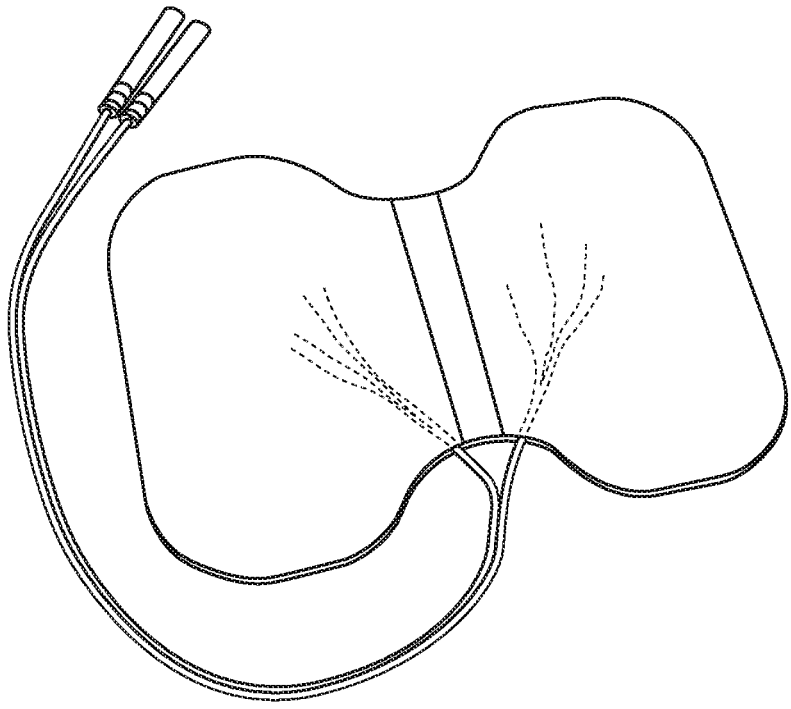
FIG. 3 depicts a conductive soft wrap which may be used with the described system.
Figure 4:
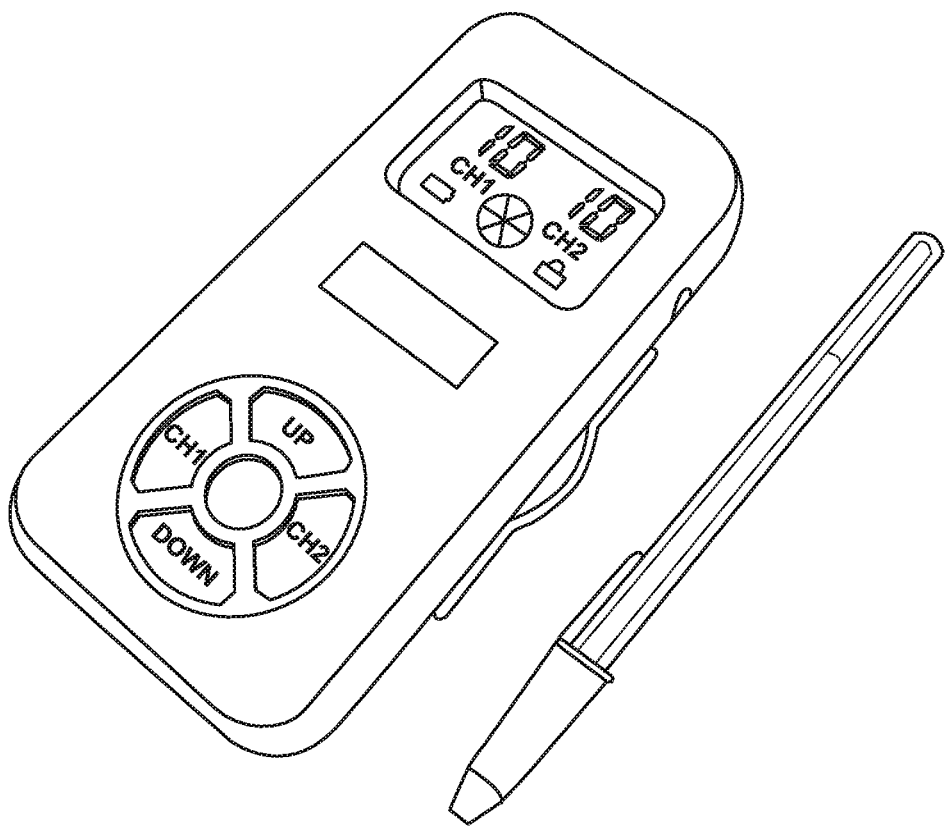
FIG. 4 depicts a programmed bioelectric stimulator depicted alongside a pen.

Referring now to FIG. 1, depicted is a stimulator for use in treating a human. The depicted device is about the size of a pen (FIG. 4) and is programmable.

A micro voltage signal generator for use herein may be produced utilizing the same techniques to produce a standard heart pacemaker well known to a person of ordinary skill in the art. An exemplary microvoltage generator is available from Mettler Electronics Corp. of Anaheim, California, US or HTM Electrônica of Amparo, BR. The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific bioelectric signals to lead to specific protein expressions at precisely the right time for, e.g., optimal treatment or for tissue regeneration.

The biostimulator of FIG. 1 is depicted with multiple soft conductive electrode pads. Electrodes may be used to deliver a bioelectric signal to the subject by applying the electrodes to the subject's skin (e.g., on the skin above the thigh muscles or on the skin above the kidneys). In certain embodiments, a bioelectric stimulator is in electrical connection with a conductive soft wrap.

A bench top stimulator (e.g., a Mettler Model 240 Stimulator from Mettler Electronics of Anaheim, CA, US) may be pre-programmed with the bioelectric signaling sequence(s) for controlling the expression and/or release of BDNF.

In some embodiments (e.g., for the regulation of the production of new neurons or new bone growth), the bioelectric signaling can further be used to modulate (e.g., upregulate) by the subject's cells the production of other molecules in addition to BDNF and/or the recruitment of stem cells. See, e.g., U.S. Pat. No. 10,960,206 to Leonhardt et al. (Mar. 30, 2021) for "Bioelectric Stimulator," the contents of which are incorporated herein by this reference.

For treating and/or preventing depression heart utilizing BDNF, see, e.g., Wu et al., "Serum Levels of FGF21, β-Klotho, and BDNF in Stable Coronary Artery Disease Patients with Depressive Symptoms: A Cross-Sectional Single-Center Study," Front. Psychiatry, 21 Jan. 2021; https://doi.org/10.3389/fpsyt.2020.587492, the contents of which is incorporated herein by this reference.

The treatment and/or prevention of depression may involve the application of further bioelectric signal(s) to upregulate expression of Klotho. See, e.g., U.S. Patent Application Publication US 2020-0289826-A1 to Leonhardt et al. (Sep. 17, 2020) for "Klotho Modulation."

Various bioelectric signals for modulating proteins are disclosed in the incorporated U.S. Pat. No. 10,960,206 to Leonhardt et al.

An implantable medical lead is described in U.S. Pat. No. 8,442,653 to Gill (May 14, 2013) for "Brain Electrode," the contents of which are incorporated herein by this reference.

Both wireless non-invasive and/or implantable wire lead ("electrode") based means may be used to deliver the regeneration and healing promoting bioelectric signal(s) to target organs such as the brain.

A wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with the described bioelectric stimulator, which can have a pacing infusion lead with, e.g., a corkscrew lead placed/attached at, e.g., the center of the tissue to be stimulated and/or treated.

The bioelectric stimulator is actuated and runs through programmed signals to signal the release of, e.g., BDNF. In such a method, the electrical signal may be measured three (3) mm deep into the tissue.

Relationship Between the Components:

The micro voltage signal generator is attached to the pacing infusion lead with, e.g., a brain electrode (Medtronic) (e.g., for bioelectric stimulation of the brain), or conductive polymer bandage or patch to the tissue or organ to be treated. An external signal programmer may be used to program the micro voltage signal generator with the proper signals for treatment including the BDNF producing signal(s). The device battery may be re-chargeable with an external battery charging wand.

The essential elements are the micro voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA cleared gel tape electrodes (Mettler) may be used for skin delivery. Electro acupuncture needles may be used to ensure the signals positively reach target tissues under the skin.

In certain preferred embodiments a method of stimulating the expression of BDNF in a living cell having a gene encoding BDNF is described, wherein the method comprises: applying to the cell a bioelectric signal of from 10 to 100 Hz at an adequate pulse width duration, wherein the amount of BDNF expression enhanced by this bioelectric signal is greater than that seen with a generic bioelectric cell stimulation alone as may be determined by an analysis of the upregulation of mRNA level/GAPDH fold gene expression in the cell in each situation.

In treating addictions, the BES is typically applied to a subject in need thereof, for 7-20 (e.g., 15 minutes per session), with three sessions per week as long as may be determined needed. Such BES therapy may be advantageously combined with other therapies (e.g., a bioelectric therapy to upregulate expression of klotho.) See, e.g., the incorporated U.S. Patent Application Publication US 2020-0289826-A1 to Leonhardt et al. (Sep. 17, 2020) for "Klotho Modulation" for particular BES therapy.

Similar BES is used to help memory, where the therapy may be combined with, for example, BES therapy to upregulate expression of klotho, SDF-1, VEGF, and eNOS. See, e.g., the incorporated U.S. Pat. No. 10,960,206 to Leonhardt et al. (Mar. 30, 2021) for "Bioelectric Stimulator" for particular BES therapy.

The invention is further described by the following illustrative Examples.

EXAMPLES

Example I

Klotho and BDNF Gene Expression in Porcine Brain Tissue

Purpose: The purpose of this study was to quantify the expression of klotho and brain-derived neurotrophic factor (BDNF) in the brain of porcine tissue (FIG. 6) after bioelectric stimulation.

Figure 5:
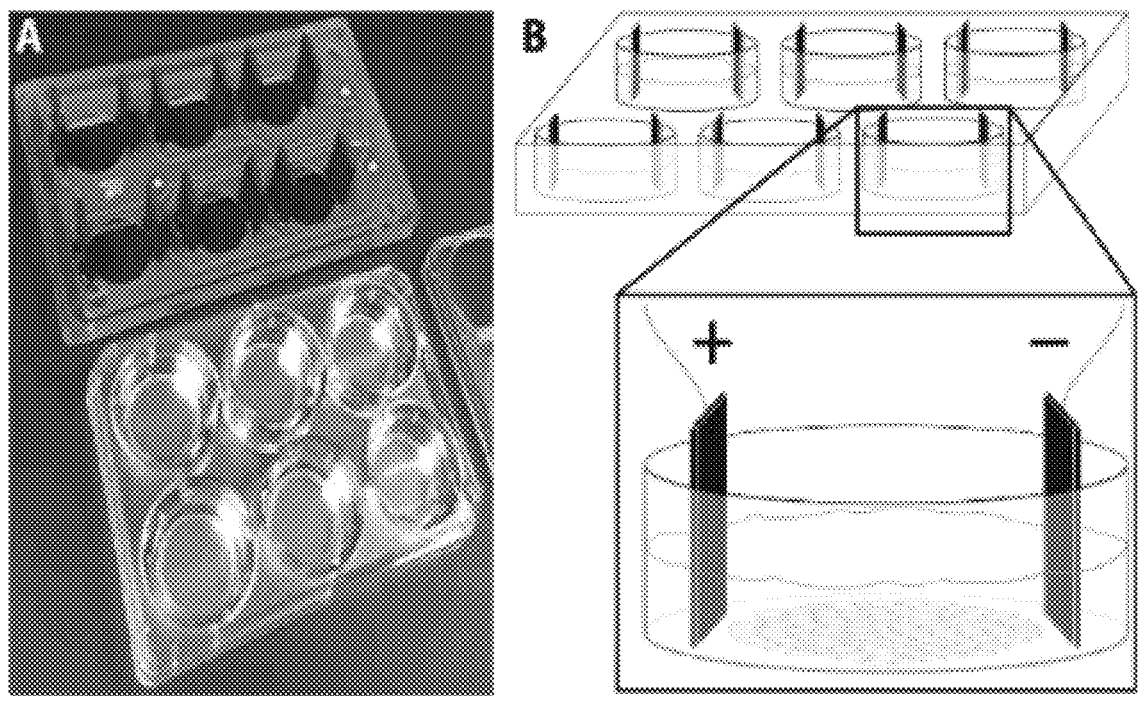
FIG. 5 depicts a bioelectric stimulation system for laboratory testing.

Electrical Signals: The tissue pieces were stimulated for 60 minutes with a Mettler stimulator, at 300 μsec pulses (FIG. 5). The current was fixed at 2 mA and frequencies ranged from 10 to 100 Hz.

Methods: Tissue received from the Midwest Swine Institute was kept in cold, ringer solution and viability of tissue was analyzed with a fluorometric detection method prior to performing this study. The porcine tissue was cut into 1-3 $mm^3$ slices and placed in a 6-well dish (FIG. 5).

FIG. 5 depicts a bioelectric stimulation system. Cells and/or tissue were plated in each dish and cultured. Stimulation occurred using an electrode array (shown at the top of panel A), which was inverted and introduced into the 6-well dish where cells were grown. Each well received uniform stimulation via a pair of carbon electrodes.

Figure 6:
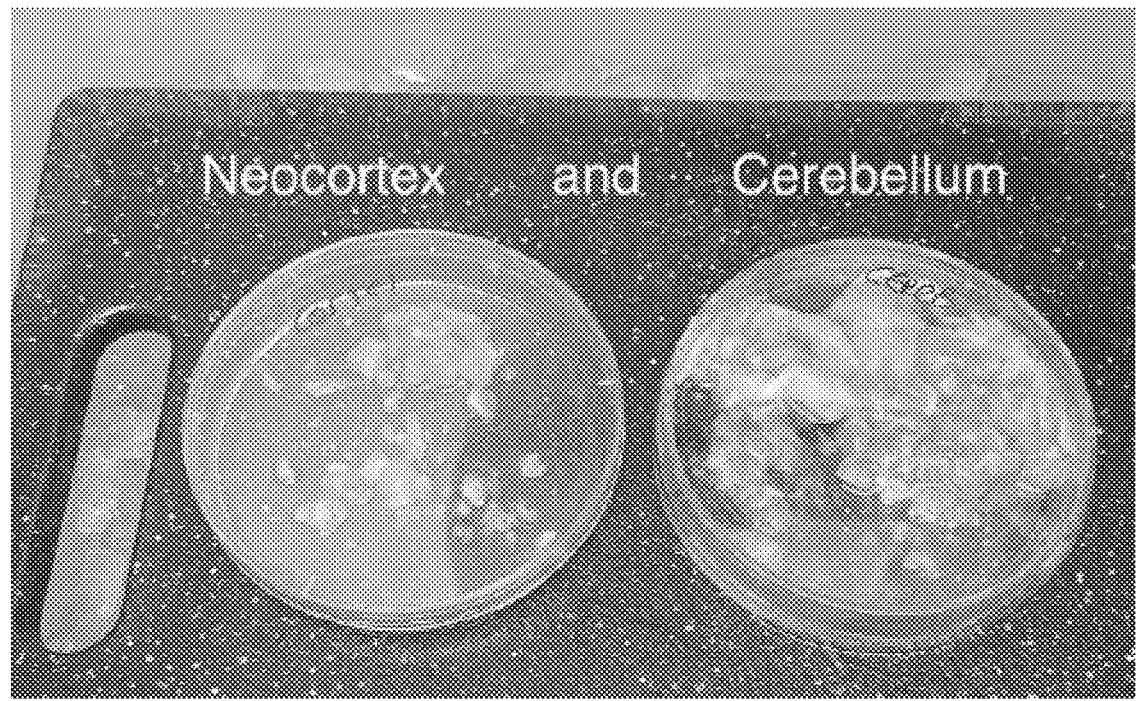
FIG. 6 is a photo of pieces of brain cortex dissociated.
Figure 7:
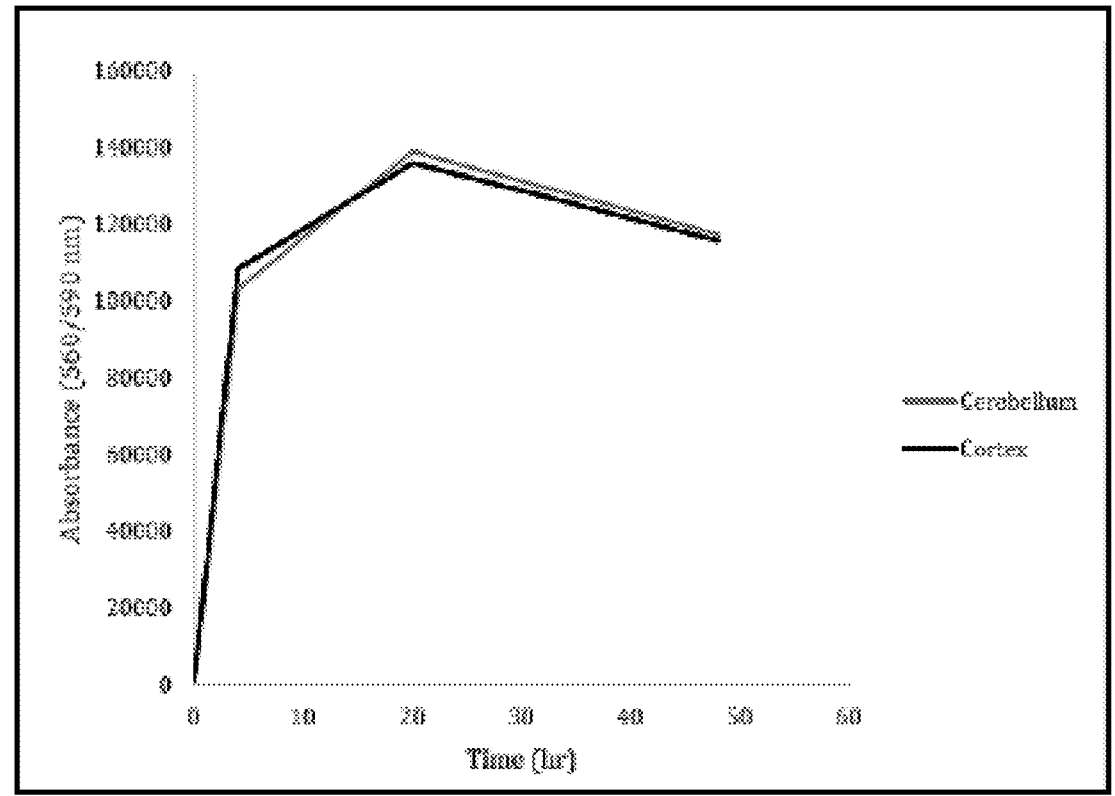
FIG. 7 is a graph comparing total enzymatic activity of porcine cerebellum and cortex tissue detected with fluorometric detection over time.

FIG. 6 is a photo of pieces of brain cortex dissociated. The dissociation of the different pieces that will be used for electrical stimulation was performed with tweezers and a scalpel while the brain tissue was inside a plastic petri dish on top of a cutting board that was cooled with ice pieces.

Bioelectric stimulation was applied to brain tissue in vitro using a commercially available Mettler stimulator (Columbus, OH, USA) via a 6-well stimulating plate interface (IONOPTIX, Westwood, MA, USA). To induce uniform electric fields in all stimulation chambers, 1.5 mL of DMEM solution (CORNING® DMEM (Dulbecco's Modified Eagle's Medium+10% Fetal Bovine Serum)) was added to each well before BES signal application Gene expression was determined by homogenizing the tissue, extracting mRNA according to the manufacturer's instructions. RNA quality was determined using a spectrophotometer and was reverse transcribed using a cDNA conversion kit. The cDNA and TaqMan qPCR Master mix was used on a 96 well plate.

Thermo Fisher data analysis software was used to calculate fold change/regulation using the delta-delta CT method, in which delta CT is calculated between the gene of interest (GOI) and an average of housekeeping genes (HKG), followed by delta-delta CT calculation (delta CT(experiment)− delta CT(control)). Fold change is then calculated using the 2^(−delta delta CT) formula.

Figure 8:
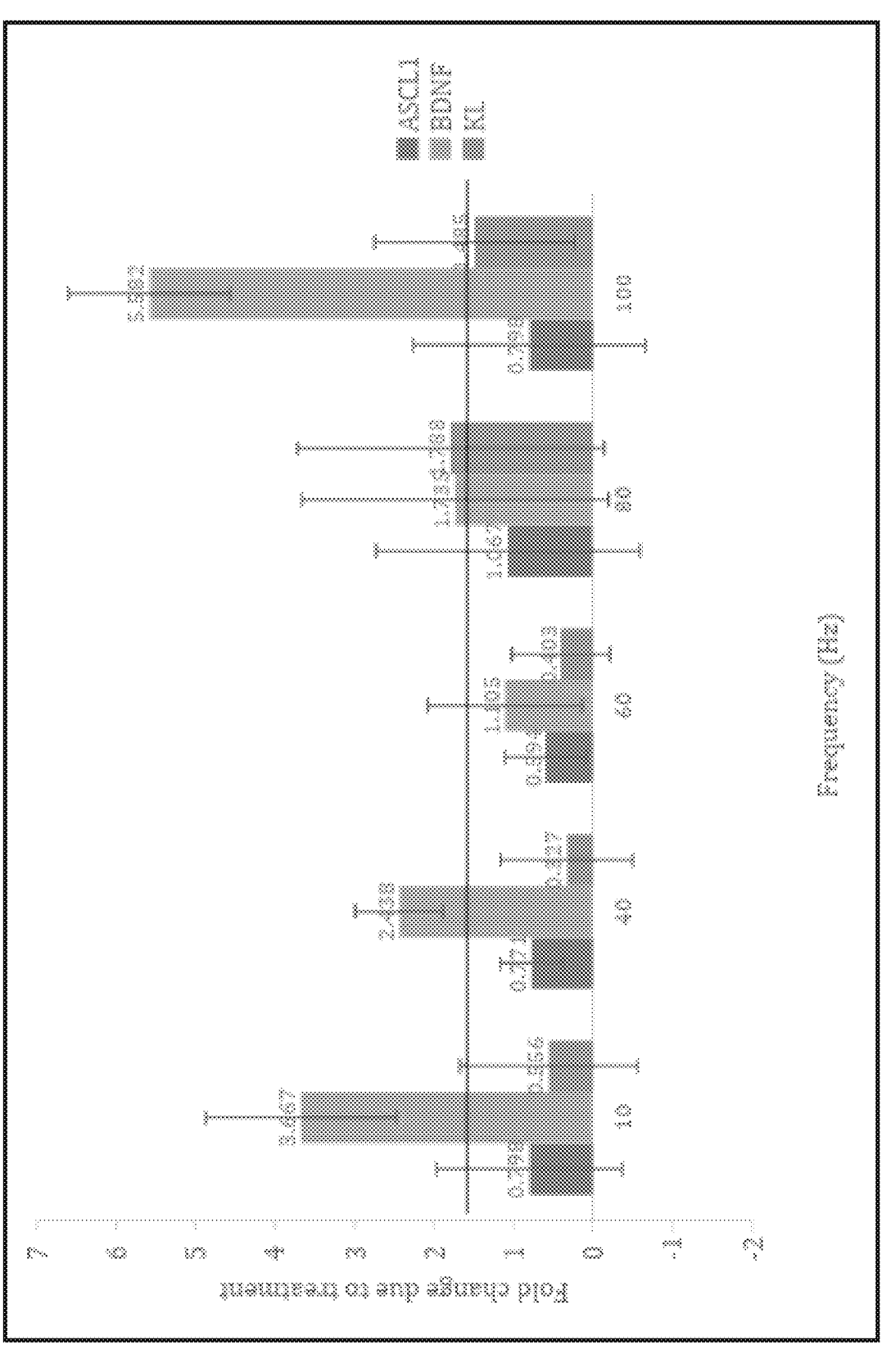
FIG. 8 is a graph depicting gene expression (fold change due treatment) of Achaete-scute homolog 1 (ASCL1), BDNF, and klotho (KL) in porcine brain tissue stimulated at 2 mA and various frequencies for 60 minutes in vitro.

Results: Among the three genes tested during these series of experiments, the expression of BDNF was the only one that reached levels beyond 2-fold (FIG. 8). This level of expression was significant after stimulating the tissue at 10 Hz and 100 Hz. The expression of Klotho (KL) did not reach the threshold of gene expression when stimulated at 2 mA and the various frequencies tested.

Discussion: In accordance with the data obtained by Thermo Fisher, at the electrical current level of 2 mA and frequencies between 10 and 100 Hz, the most significant increase in expression was that of BDNF.

Klotho also increased its expression, but the levels were lower than the 2-fold threshold, with high variability in the data.

At this time, it cannot be determined which cells are responding to the increase of expression of BDNF in the brain, but this can be clarified with the use of enzymatically isolated cells from this tissue. Although autocrine and paracrine interactions will not be in effect in an isolated cell line.

Conclusions:

1) At 2 mA and 10 Hz or 100 Hz stimulation, BDNF is significantly expressed in neocortex tissue.

2) Expression can be optimized by using higher current and other frequencies closer to the ones used during the experiments performed in this Example.

Example II

Bioelectric stimulation of the gray matter of porcine neocortex with bioelectric signals of 1 Hz, 40 Hz, and 100 Hz, each at 2 mA (as measured at the level of the cell), for 60 minutes similar to that described for Example I caused the stimulated cellular tissue to exhibit enhanced expression of BDNF in comparison to a cell not so stimulated.

Example III

Downregulation of Expression of BDNF and IGF1 and Upregulation of Expression of GDF10

Purpose: The aim of the study was to profile the gene expression of several key molecules involved in the pathophysiology of depression and other neurodegenerative disorders (e.g., BDNF, IGF1, klotho and GDF10) before and after bioelectric stimulation and measured by RT-qPCR. The study was carried out by stimulating porcine neocortex tissue by applying precise bioelectric signals to cellular tissue for 20 minute durations and then analyzing the changes in gene expression, normalized to a stable housekeeping gene.

Electrical Signals: For purposes of this Example, porcine neocortex tissue was stimulated for 20 minutes with a Mettler Systim240 under the following conditions:

| Current (mA) | Frequency (Hz) | Pulse width (μsec) |
|---|---|---|
| 2 | 20 | 1,000 |
| 2 | 20 | 300 |
| 2 | 10 | 300 |
| 3 | Direct Current (positive) | Not Applicable |
| 2 | Direct Current (positive) | Not Applicable |
| 2 | 30 | 1,000 |
| 2 | 30 | 300 |

Methods: The neocortex tissue was received from California Medical Innovations Institute in San Diego, California, US, and was kept in cold, saline solution and viability of tissue was analyzed with a fluorometric detection method before performing this study.

Bioelectric stimulation was applied to 2-3 mm pieces of the porcine neocortex tissue in vitro using a commercially available Mettler Systim240 via a 6-well stimulating plate interface (IONOPTIX®, Westwood, MA, US). To induce uniform electric fields in all stimulation chambers, 1.3 mL of Dulbecco's Modified Eagle Medium (DMEM) solution was added to each well before application of the bioelectric stimulation (BES) signal.

A bioelectric stimulation system of FIG. 5 was used. Cellular tissue was placed in each well and was stimulated using an electrode array (shown at the top of panel A of the figure), which was inverted and introduced into the 6-well dish. Each well received uniform stimulation via a pair of carbon electrodes positioned at opposite sides (panel B of the figure).

Gene expression was determined by homogenizing the tissue and extracting mRNA according to the manufacturer's instructions. RNA quality was determined using a spectrophotometer and was reverse transcribed using a cDNA conversion kit. The cDNA and TaqMan qPCR Master mix was plated on a 96 well plate.

THERMOFISHER® data analysis software was used to calculate fold change/regulation using the delta-delta CT method, in which delta CT is calculated between the gene of interest (GOI) and an average of housekeeping genes (HKG), followed by delta–delta CT calculation (delta CT(experiment)–delta CT(control)). Fold change is then calculated using the $2^\wedge(-\text{delta delta CT})$ formula.

Figure 9:
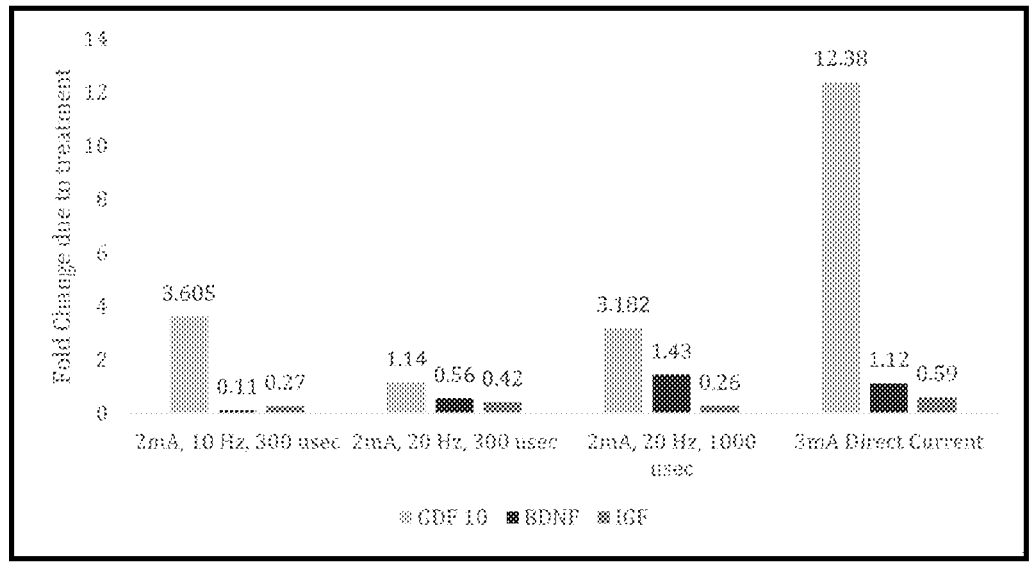
FIG. 9 includes sets of bar graphs depicting gene expression (fold change in gene expression due to treatment) of GDF10, BDNF, and insulin-like growth factor 1 ("IGF"), respectively, in porcine neocortex tissue stimulated with bioelectric signals of (1) 2 mA, 10 Hz, and 300 μsec (pulse width), (2) 2 mA, 20 Hz, 300 μsec; (3) 2 mA, 20 Hz, 1,000 μsec; and (4) 3 mA Direct Current ("DC") for 20 minutes.
Figure 10:
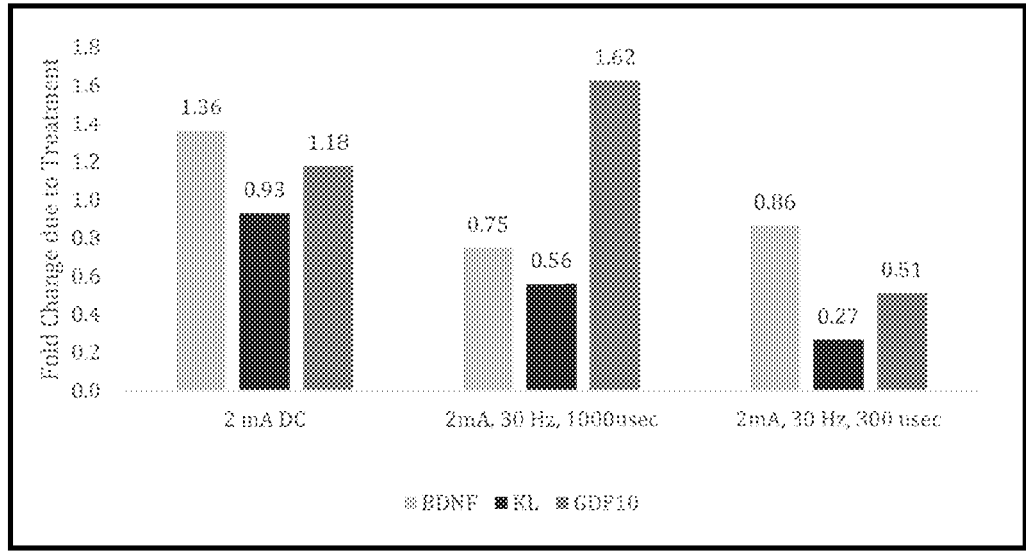
FIG. 10 includes sets of bar graphs depicting gene expression (fold change in gene expression due to treatment) of BDNF, KL, and GDF10, respectively, in porcine neocortex tissue stimulated with bioelectric signals of (1) 2 mA DC, (2) 2 mA, 30 Hz, 1,000 μsec (pulse width); and (3) 2 mA, 30 Hz, 300 μsec for 20 minutes.

Results: The results depicted in FIGS. 9 and 10 indicate that there are some genes that increase (upregulate) expression post-stimulation and others that decrease (downregulate) expression.

A 20 minute stimulation at 3 mA direct current, resulted in a 12-fold increase of Growth differentiation factor 10 ("GDF10," also known as bone morphogenetic protein 3B "BMP-3B"). However, the expression of BDNF and insulin-like growth factor 1 ("IGF-1" or "IGF") did not increase past the 2-threshold of gene expression. Expression of BDNF and IGF was decreased.

Discussion: The expression of GDF10 is seen to increase following the stimulation of the applied parameters. Prior studies on the gray matter of porcine neocortex (see, e.g., Example II) showed enhanced expression of BDNF at 1 Hz, 40 Hz, and 100 Hz, 2 mA, stimulated for 60 minutes.

The various cell types present in the stimulated tissue should be further studied. Myelin forming cells and endothelial cells are the cells that generally express BDNF and other growth factors. Further investigation of stimulation parameters including duration of stimulation, interactions, and pathways would be beneficial.

Conclusions: The BES protocol applied to porcine neocortex tissue induced the upregulation of expression of GDF10. The same BES protocol downregulated the expression of BDNF and IGF. Certain cell types express specific genes and factors, further investigation is needed in the cell types present in the stimulated tissue.

REFERENCES (The contents of the entirety of each of which is incorporated herein by this reference.)

Feng et al. "Secretion of nerve growth factor, brain-derived neurotrophic factor, and glial cell-line derived neurotrophic factor in co-culture of four cell types in cerebrospinal fluid-containing medium" *Neural Regen Res.* 2012 Dec. 25; 7(36):2907-14. doi: 10.3969/j.issn.1673-5374.2012.36.008. PMID: 25317143; PMCID: PMC4190949.

Jiao et al. "Brain-derived neurotrophic factor protects against tau-related neurodegeneration of Alzheimer's disease" *Transl Psychiatry.* 2016 Oct. 4; 6(10):e907. doi: 0.1038/tp.2016.186. PMID: 27701410; PMCID: PMC5315549.

Sato et al. "White matter activated glial cells produce BDNF in a stroke model of monkeys." *Neurosci Res.* 2009

September; 65(1):71-8. doi: 10.1016/j.neures.2009.05.010. Epub 2009 Jun. 6. PMID: 19501123.

Wu et al., "Serum Levels of FGF21, β-Klotho, and BDNF in Stable Coronary Artery Disease Patients with Depressive Symptoms: A Cross-Sectional Single-Center Study," *Front. Psychiatry*, 21 Jan. 2021; https://doi.org/10.3389/fpsyt.2020.587492.

Xiong et al. "Neurotrophins induce BDNF expression through the glutamate receptor pathway in neocortical neurons" *Neuropharmacology*. 2002 June; 42(7): 903-912.

U.S. Pat. No. 8,442,653 to Gill (May 14, 2013) for "Brain Electrode."

U.S. Patent Application Publication US 2020-0289826-A1 to Leonhardt et al. (Sep. 17, 2020) for "Klotho Modulation."

U.S. Pat. No. 10,960,206 to Leonhardt et al. (Mar. 30, 2021) for "Bioelectric Stimulator."

What is claimed is:

1. A method of treating a subject for Alzheimer's disease, schizophrenia, post-traumatic stress disorder, addiction(s), and/or depression using a bioelectric stimulator comprising an electric signal generator and electrode(s), which electric signal generator is programmed to produce at least one bioelectric signal that stimulates target tissue comprising living cells of the subject to upregulate expression and/or release of brain-derived neurotrophic factor (BDNF) by the living cells, wherein the bioelectric signal comprises, within 15%, a bioelectric signal having a biphasic pulse at a frequency selected from the group consisting of 1 Hz, 10 Hz, 40 Hz, 80 Hz, and 100 Hz, with a pulse width of either about 300 microseconds or about 1,000 microseconds, and a current of about 2 mA as may be measured at the cellular level to stimulate target tissue comprising the living cells of the subject, the method comprising:

administering the bioelectric signal to the living cells via the electrode(s) for at least 5 minutes to about an hour, so as to upregulate the expression of BDNF by the living cells so as to treat the subject for Alzheimer's disease, schizophrenia, post-traumatic stress disorder, addiction(s), and/or depression.

2. The method according to claim 1, wherein the bioelectric signal has, within 15%, a biphasic pulse at a frequency selected from the group consisting of 1 Hz, 10 Hz, 40 Hz, 80 Hz, and 100 Hz, which bioelectric signal upregulates expression of BDNF by the living cells of the target tissue.

3. The method according to claim 2, wherein the bioelectric signal has a frequency of about 1 Hz.

4. The method according to claim 2, wherein the bioelectric signal has a frequency of about 40 Hz.

5. The method according to claim 2, wherein the bioelectric signal has a frequency of about 80 Hz.

6. The method according to claim 2, wherein the bioelectric signal has a frequency of about 100 Hz.

7. The method according to claim 1, wherein the target tissue comprises gray matter of the neocortex.

8. The method according to claim 1, wherein the bioelectric signal is administered for about 60 minutes.

9. The method according to claim 1, wherein the bioelectric signal comprises about 10 Hz and about 300 microseconds pulse width.

10. The method according to claim 1, wherein the upregulation of BDNF expression comprises at least a 2-fold increase in BDNF expression relative to an unstimulated control.

11. The method according to claim 1, wherein upregulation of BDNF is determined by analysis of mRNA expression normalized to a housekeeping gene.

12. The method according to claim 1, wherein the bioelectric stimulator is external to the subject.

13. The method according to claim 1, wherein the bioelectric signal is delivered wirelessly to the target tissue.

14. The method according to claim 1, further comprising administering stem cells to the subject.

* * * * *